(12) United States Patent
Rader et al.

(10) Patent No.: US 11,497,613 B2
(45) Date of Patent: Nov. 15, 2022

(54) MIDFOOT BONE REPLACEMENT IMPLANT

(71) Applicant: TMR Orthopedics, LLC, Henryville, IN (US)

(72) Inventors: Andrew J. Rader, Jasper, IN (US); D. Matthew Michael, Henryville, IN (US)

(73) Assignee: TMR Orthopedics, LLC, Henryville, IN (US)

( * ) Notice: Subject to any disclaimer, the term of this patent is extended or adjusted under 35 U.S.C. 154(b) by 21 days.

(21) Appl. No.: 16/779,244

(22) Filed: Jan. 31, 2020

(65) Prior Publication Data

US 2021/0177616 A1 Jun. 17, 2021

Related U.S. Application Data

(60) Provisional application No. 62/948,341, filed on Dec. 16, 2019.

(51) Int. Cl.
*A61F 2/42* (2006.01)
*A61F 2/30* (2006.01)

(52) U.S. Cl.
CPC .. *A61F 2/4225* (2013.01); *A61F 2002/30138* (2013.01); *A61F 2002/30159* (2013.01); *A61F 2002/30784* (2013.01)

(58) Field of Classification Search
CPC .... A61F 2/4225; A61F 2/4241; A61F 2/4455; A61F 2/446; A61F 2/4465; A61F 2/447
See application file for complete search history.

(56) References Cited

U.S. PATENT DOCUMENTS

| | | | |
|---|---|---|---|
| 8,636,808 B2 | 1/2014 | Olson | |
| 8,920,476 B2 | 12/2014 | Tyber et al. | |
| 9,867,642 B2 | 1/2018 | Simon | |
| 9,943,347 B2 | 4/2018 | Wayne et al. | |
| 2005/0065607 A1* | 3/2005 | Gross | A61F 2/447 623/17.11 |
| 2008/0154375 A1* | 6/2008 | Serhan | A61F 2/441 623/17.16 |
| 2009/0005870 A1* | 1/2009 | Hawkins | A61F 2/442 623/17.11 |
| 2016/0158023 A1* | 6/2016 | Klimek | A61F 2/442 623/17.16 |
| 2016/0184099 A1* | 6/2016 | Gotfried | A61F 2/2846 623/18.11 |
| 2016/0338843 A1* | 11/2016 | Mangione | A61B 17/562 |
| 2017/0056031 A1* | 3/2017 | Awtrey | A61B 6/485 |

* cited by examiner

*Primary Examiner* — Marcia L Watkins
(74) *Attorney, Agent, or Firm* — Maginot, Moore & Beck LLP (57) ABSTRACT

An implant for a human includes a body having a superior surface, an inferior surface, a distal surface, and a proximal surface. The proximal surface is configured to engage the talus and the calcaneus of an adult human, and the distal surface configured to engage at least the first and fourth metatarsals of the adult human. The distal surface has a largest distal height and a largest distal width that is greater than the largest distal height, and the proximal surface has a largest proximal height and a largest proximal width that is greater than the largest proximal height.

20 Claims, 11 Drawing Sheets

MIDFOOT BONE REPLACEMENT IMPLANT

CLAIM OF PRIORITY

This application claims the benefit of priority to U.S. Provisional Application No. 62/948,341, filed Dec. 16, 2019, the contents of which are incorporated herein by reference in their entirety.

TECHNICAL FIELD

This disclosure relates generally to surgical implants, and more specifically to surgical implants for replacing midfoot bones of a patient.

BACKGROUND

Charcot neuropathic osteoarthropathy (CN), commonly referred to as the Charcot foot, is a condition causing weakening of the bones in the foot that can occur in people who have significant nerve damage (neuropathy). More particularly, Charcot foot is commonly found in diabetic patients, with between 1 and 5 percent of diabetic patients developing Charcot foot, though this number may be higher due to Charcot foot frequently going undiagnosed. The weakening of the midfoot bones causes dislocations and fractures in the midfoot bones. Left untreated, Charcot foot can result in the foot developing a rocker-bottom shape, which can cause severe health complications and potentially require amputation of the foot.

Currently there are a number of solutions for fixating and fusing bones of the midfoot to assist in bone healing and repair of Charcot foot. Some of these solutions attempt to repair midfoot bones by fixating implants or devices and bones to one another or to the calcaneus or talus, or to fixate or fuse bones by means of external fixation. However, fixing the bones to one another or externally fixating the bones requires subsequent surgical interventions to add and/or remove additional hardware, can cause patient emotional and physical decline, and require prolonged recovery periods. Moreover, such methods are reliant on the bone quality or sustainability of the structures of the midfoot, which may be compromised or deteriorate due to progression of the Charcot foot disease. In addition, conventional internal or external fixation surgeries are very costly and may be avoided by patients due to the cost, insurance and/or patient cost load, extensive procedure and recovery time, liability concerns, and poor outcomes.

Another solution to Charcot foot is to attempt to fixate some of the midfoot bones to bones of the hindfoot or forefoot. However, fixating bones to the hindfoot or forefoot still rely on the diseased bones and/or joints to maintain sufficient bone quality for fixation, often require subsequent surgeries with prolonged recovery periods, and can also be very costly for the patient, insurance provider, surgeons, and the hospitals.

Moreover, the known surgical remedies for Charcot foot are often unsuccessful, and may result in irreparable damage to the midfoot region and the adjacent bones, which requires amputation of the foot. Amputation, however, often results in the patient's health deteriorating due to surgical complications or the inability of the patient to engage in physical activity after amputation of the foot, with studies showing a 73% 5-year mortality rate after diabetic foot amputation.

What is needed, therefore, is a device that can improve patient outcomes, increase the stability of feet impacted by Charcot foot, reduce the number and length of surgical procedures to treat Charcot foot, and reduce the cost of treating Charcot foot.

SUMMARY

In one embodiment, an implant for a human includes a body having a superior surface, an inferior surface, a distal surface, and a proximal surface. The proximal surface is configured to engage the talus and the calcaneus of an adult human, and the distal surface configured to engage at least the first and fourth metatarsals of the adult human. The distal surface has a largest distal height and a largest distal width that is greater than the largest distal height, and the proximal surface has a largest proximal height and a largest proximal width that is greater than the largest proximal height.

In another embodiment, a method of implanting a midfoot implant in an adult human foot includes removing cuneiform, cuboid, and navicular bones from the adult human foot and inserting a midfoot implant having a body into the adult human foot such that a proximal surface of the body engages a calcaneus and a talus of the adult human foot, and a distal surface of the body engages a first metatarsal and a fourth metatarsal of the adult human foot. The distal surface has a largest distal height and a largest distal width, which is greater than the largest distal height, and the proximal surface has a largest proximal height and a largest proximal width, which is greater than the largest proximal height.

In a further embodiment, a kit comprises a first implant for a human midfoot, which comprises a body having a superior surface, an inferior surface, a distal surface, and a proximal surface. The proximal surface is configured to connect to the talus and the calcaneus of an adult human, and the distal surface configured to connect to at least the first and fourth metatarsals of the adult human. The distal surface has a largest distal height and a largest distal width that is greater than the largest distal height, and the proximal surface has a largest proximal height and a largest proximal width that is greater than the largest proximal height. The kit further includes at least two fixating fasteners configured to affix the body to the talus, calcaneus, and the first and fourth metatarsals.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one skilled in the art to which this document pertains.

The terms "comprising," "including," "having," and the like, as used with respect to embodiments of the disclosure, are synonymous. As used herein, the term "approximately" is to be interpreted to encompass the range that one of ordinary skill in the art would consider reasonable in the context of the particular use of the term. Alternatively, the term "approximately" may be interpreted to include all values that are within ±10% of the reference value.

Figure 1:
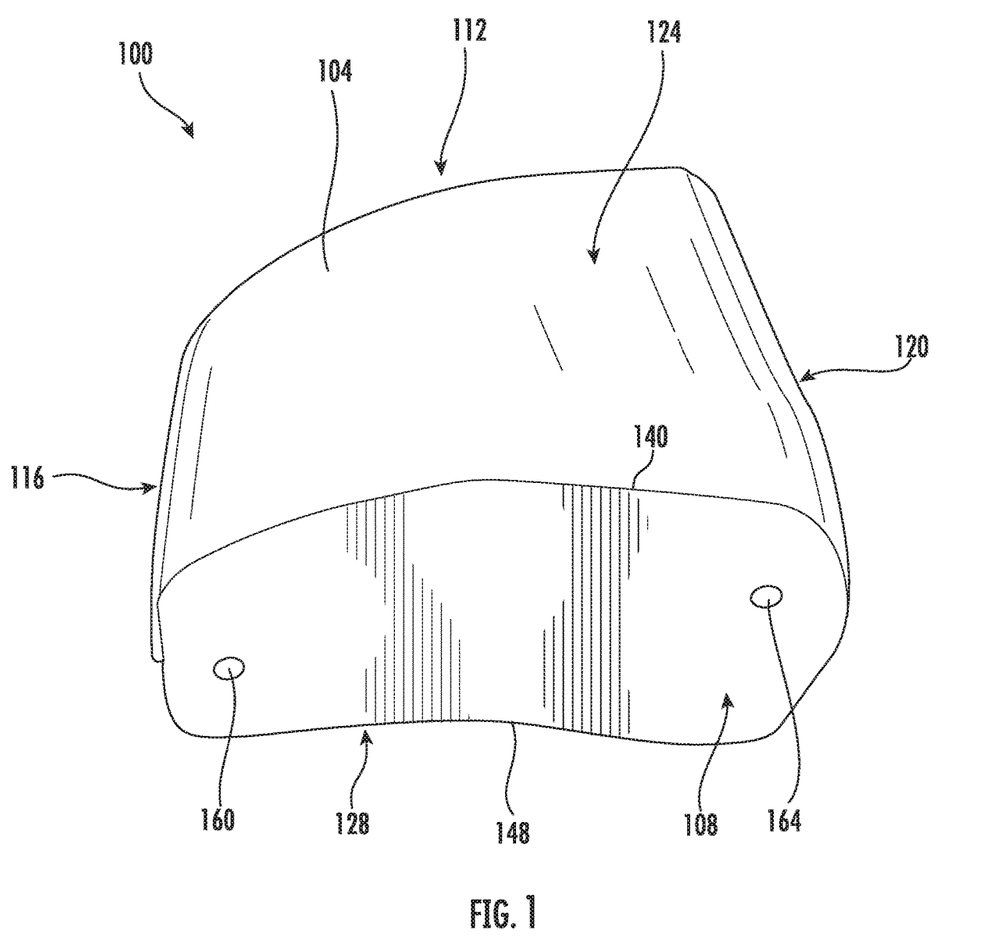
FIG. 1 is a superior-proximal perspective view of a midfoot implant.

FIG. 1 depicts a first embodiment of a midfoot implant 100 that replaces bones in the midfoot region of an adult human patient's foot so as to stabilize the patient's midfoot region. While the illustrated midfoot implant 100 is configured for implantation in a patient's left foot, the reader should appreciate that the midfoot implant can be mirrored about the proximal-distal plane for use in a patient's right foot. The midfoot implant 100 is a solid body 104 formed of a rigid biocompatible material. In one embodiment, the solid body 104 of the midfoot implant 100 is formed of a rigid biocompatible polymer that may, for example, be formed by an additive process, such as three-dimensional printing, by a casting process, or by a subtractive process, such as milling. The solid body 104 of the midfoot implant 100 has a proximal end surface 108, a distal end surface 112, a medial side surface 116, a lateral side surface 120, a superior surface 124, and an inferior surface 128.

In the illustrated embodiment, the solid body 104 is integrally formed as a single piece of material, for example as a monolithic body. In other embodiments, the solid body 104 of the midfoot implant may be formed of two or more pieces of material. More particularly, the proximal end surface 108 and the distal end surface 112 may be on different pieces of material.

Figure 2:
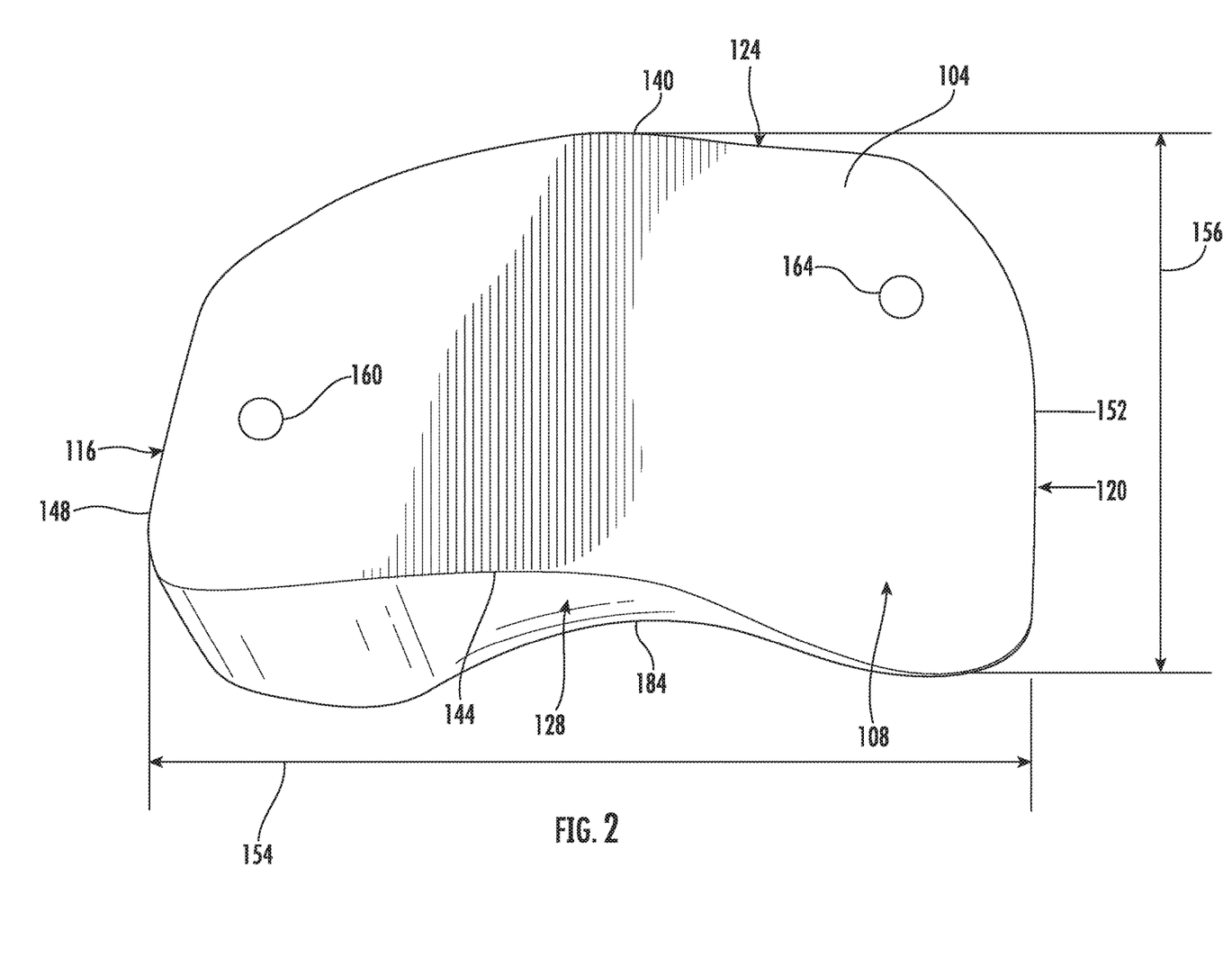
FIG. 2 is a proximal plan view of the midfoot implant of FIG. 1.

As depicted in FIG. 2, the proximal end surface 108 is defined by a convex superior edge 140, a concave inferior edge 144, a medial edge 148, and a lateral edge 152. In the illustrated embodiment, the proximal end surface 108 is substantially planar, though the reader should appreciate that in other embodiments the proximal end surface may be shaped so as to conform to the talus and calcaneus bones of the patient's foot. More particularly, in some embodiments, the distal end surface 112 may include one or more protuberances or indentations that conform to one or more of the calcaneus and talus bones of the patient. In some embodiments, the proximal end surface 108 may be smooth, though in other embodiments, the proximal end surface 108 may have a roughened lattice-like or web-like structure that is porous and rough.

The proximal end surface 108 has a largest width 154 measured from the outermost part of the medial edge 148 to the outermost part of the lateral edge 152 and a largest height 156 measured from the uppermost part of the convex upper edge 140 to the lowermost part of the concave lower edge 144. The largest width 154 is greater than the largest height 156 or, in other words, the proximal end surface 108 is wider than it is tall, so as to conform generally to the anatomical shape of the midfoot region of the patient's foot.

The proximal end surface 108 also defines the proximal ends of two through-holes 160, 164, one of which is on the medial side and the other of which is on the lateral side of the proximal end surface 108. As will be described in detail below, the medial through-hole 160 is extends from the talus to the first metatarsal of a patient, while the lateral through-hole 164 extends from the calcaneus to the fourth metatarsal of the patient. The proximal end of the medial through-hole 160 is therefore arranged vertically in a middle third, more particularly approximately halfway, between the uppermost portion of the convex superior edge 140 and the lowermost portion of the concave inferior edge 144, and spaced apart from the medial edge 148 by a distance of between approximately 5% and approximately 20% of the largest width 154, and in one particular embodiment, approximately 12.5% of the largest width 154. The proximal end of the lateral through-hole 164 is arranged vertically in the upper third of the proximal end surface 108, and spaced apart from the lateral edge 152 by a distance of between approximately 10% to approximately 25% of the largest width 154, and in one particular embodiment, approximately 15% of the largest width 154.

Figure 3:
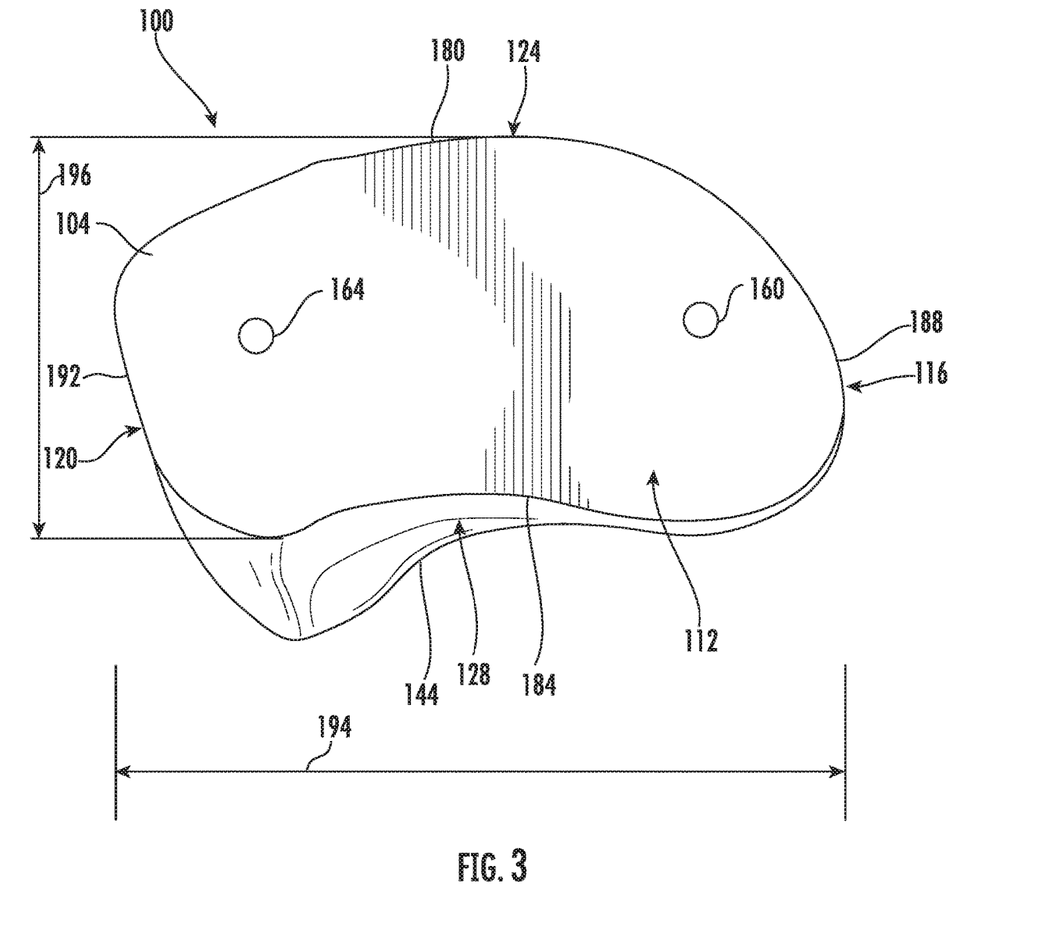
FIG. 3 is a distal plan view of the midfoot implant of FIG. 1.

FIG. 3 illustrates the distal end surface 112 of the midfoot implant 100. The distal end surface 112 is defined by a convex superior edge 180, a concave inferior edge 184, a medial edge 188, and a lateral edge 192. Again, the distal end surface 112 of the illustrated embodiment is substantially planar, though the reader should appreciate that in other embodiments the distal end surface 112 may be shaped so as to conform to one or more of the metatarsals of the patient, and more particularly to the first and fourth metatarsals. Additionally, in some embodiments, the distal end surface 112 may include one or more protuberances or indentations that conform to one or more of the metatarsals of the patient. In some embodiments, the distal end surface 112 may be smooth, though in other embodiments, the distal end surface 112 may have a roughened lattice-like or web-like structure that is porous and rough.

The distal end surface 112 has a largest width 194 measured from the outermost portion of the medial edge 188 to the outermost portion of the lateral edge 192 and a largest height 196 measured from the uppermost part of the convex superior edge 180 to the lowermost part of the concave inferior edge 184. The largest width 194 is greater than the largest height 196 or, in other words, the distal end surface 112 is wider than it is tall. Additionally, the largest width 194 and largest height 196 of the distal end surface 112 are less than the respective largest width 154 and largest height 156 of the proximal end surface 108. Thus, the midfoot implant 100 generally conforms to the anatomical shape of a patient's midfoot region.

The distal end surface 112 defines the distal ends of the through-holes 160, 164. In particular, the distal end of the medial through-hole 160 is located vertically in a middle third, more particularly approximately halfway, between the uppermost portion of the convex superior edge 180 and the lowermost portion of the concave inferior edge 184, and is spaced apart from the medial edge 188 by a distance of between approximately 15% and approximately 25% of the largest width 194 of the distal end surface 112, and in one particular embodiment approximately 20% of the largest width 194. The distal end of the lateral through-hole 164 is also located vertically in a middle third, more particularly approximately halfway, between the uppermost portion of the convex superior edge 180 and the lowermost portion of the concave inferior edge 184, and is spaced apart from the lateral edge 192 by a distance of between approximately 15% and approximately 25% of the largest width 194 of the distal end surface 112, and in one particular embodiment approximately 20% of the largest width 194.

Figure 4:
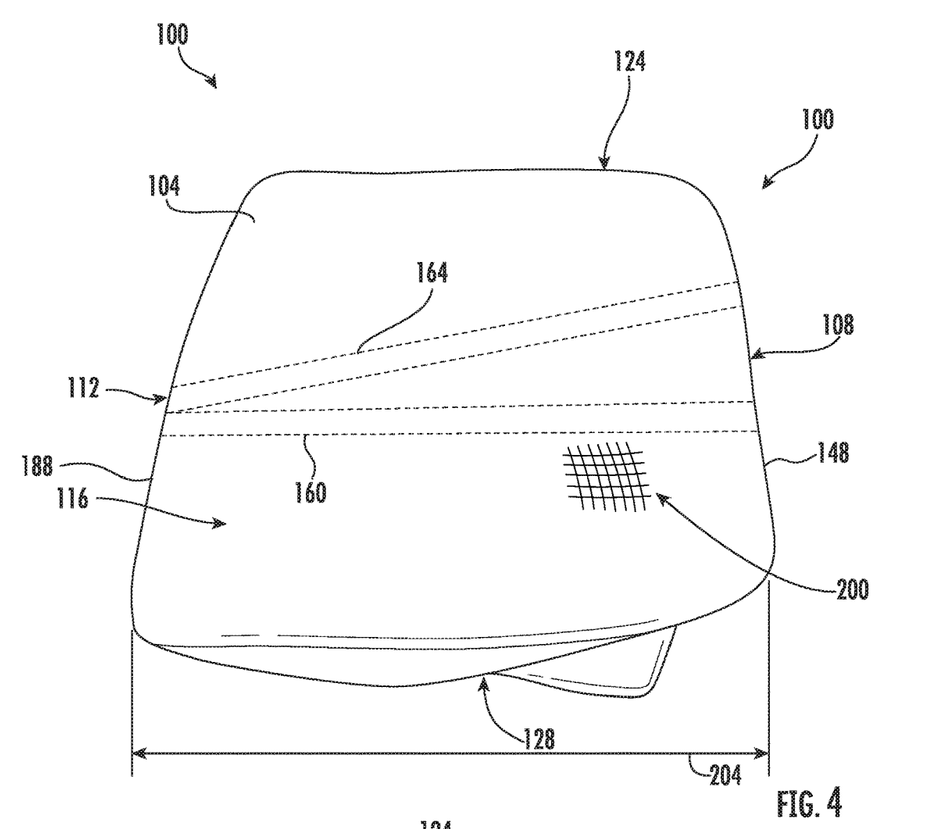
FIG. 4 is a medial side plan view of the midfoot implant of FIG. 1.
Figure 5:
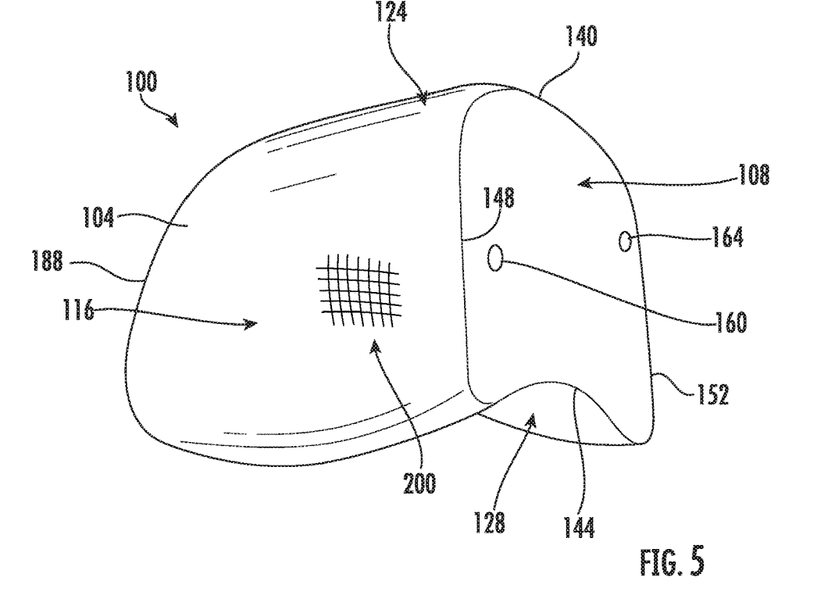
FIG. 5 is a medial-proximal perspective view of the midfoot implant of FIG. 1.

FIGS. 4 and 5 illustrate the medial side surface 116 of the midfoot implant 100. The medial side surface 116 is defined on the proximal end by the medial edge 148 of the proximal end surface 108 and on the distal end by the medial edge 188 of the distal end surface 112. On the superior and inferior sides, the medial side surface 116 blends smoothly into the respective superior surface 124 and inferior surface 128.

In some embodiments, a portion or the entirety of the medial side surface 116 may include a lattice-like or web-like outer structure 200 that is porous and rough. In other embodiments, the entire medial side surface 116 may be smooth and solid.

The medial side surface 116 defines a medial side maximum length 204 spanning from the furthest proximal portion of the medial edge 148 of the proximal end surface 108 to the furthest distal portion of the medial edge 188 of the distal end surface 112. The medial side maximum length 204 may be, for example, between approximately 2 cm and approximately 4 cm. In one particular embodiment, the medial side maximum length 204 may be approximately 2 cm shorter than the medial side length of an average adult human midfoot, or approximately 3 cm, to allow the midfoot implant 100 to be used in a variety of patients.

Figure 6:
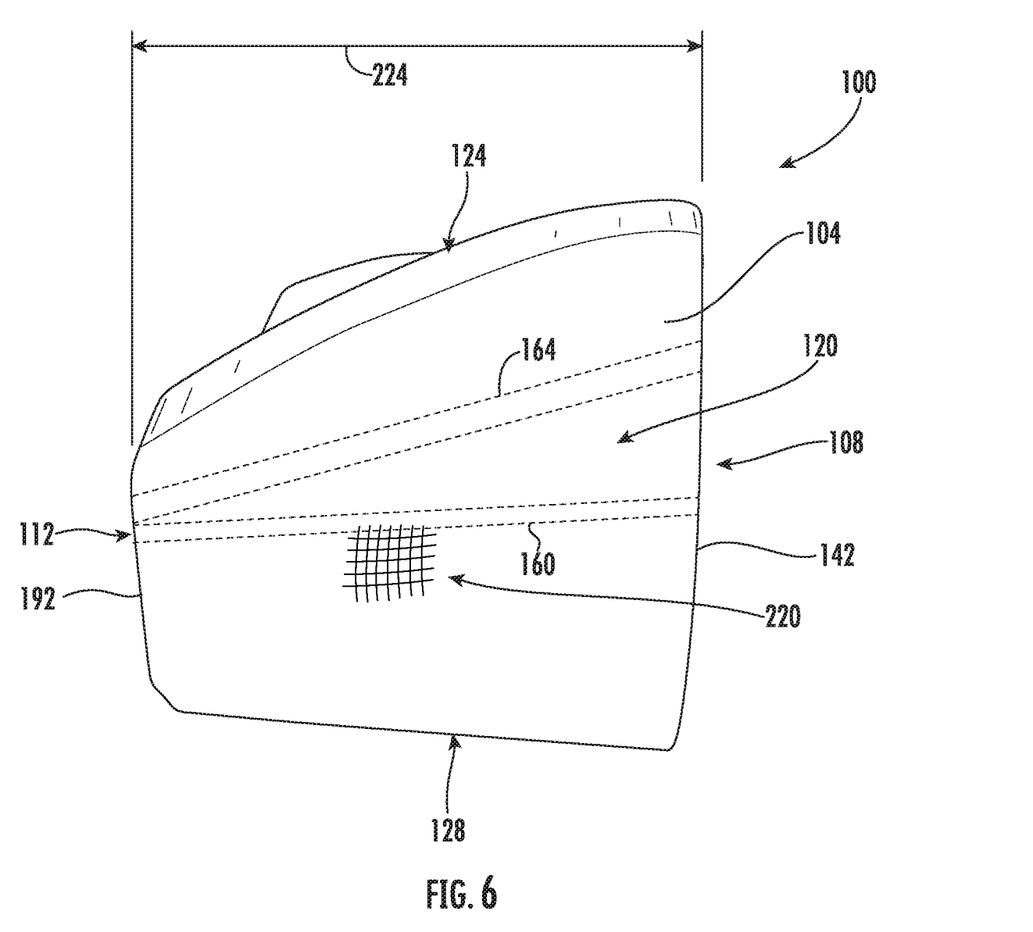
FIG. 6 is a lateral side plan view of the midfoot implant of FIG. 1.

FIG. 6 illustrates the lateral side surface 120 of the midfoot implant 100. The lateral side surface 120 is defined on the proximal end by the lateral edge 152 of the proximal end surface 108, and on the distal end by the lateral edge 192 of the distal end surface 112. As with the medial side surface 116, the lateral side surface 120 may, in some embodiments, include a lattice-like or web-like outer structure 220 that is porous and rough. In other embodiments, the entire lateral side surface 120 may be smooth and solid.

The lateral side surface 120 defines a lateral side maximum length 224 spanning from the furthest proximal portion of the lateral edge 152 of the proximal end surface 108 to the furthest distal portion of the lateral edge 192 of the distal end surface 112. The lateral side maximum length 224 may be, for example, between approximately 3 cm and approximately 5 cm. In one particular embodiment, the lateral side maximum length 224 may be approximately 2 cm shorter than the lateral side length of an average adult human midfoot, or approximately 4 cm, to allow the midfoot implant 100 to be used in a variety of patients.

Figure 7:
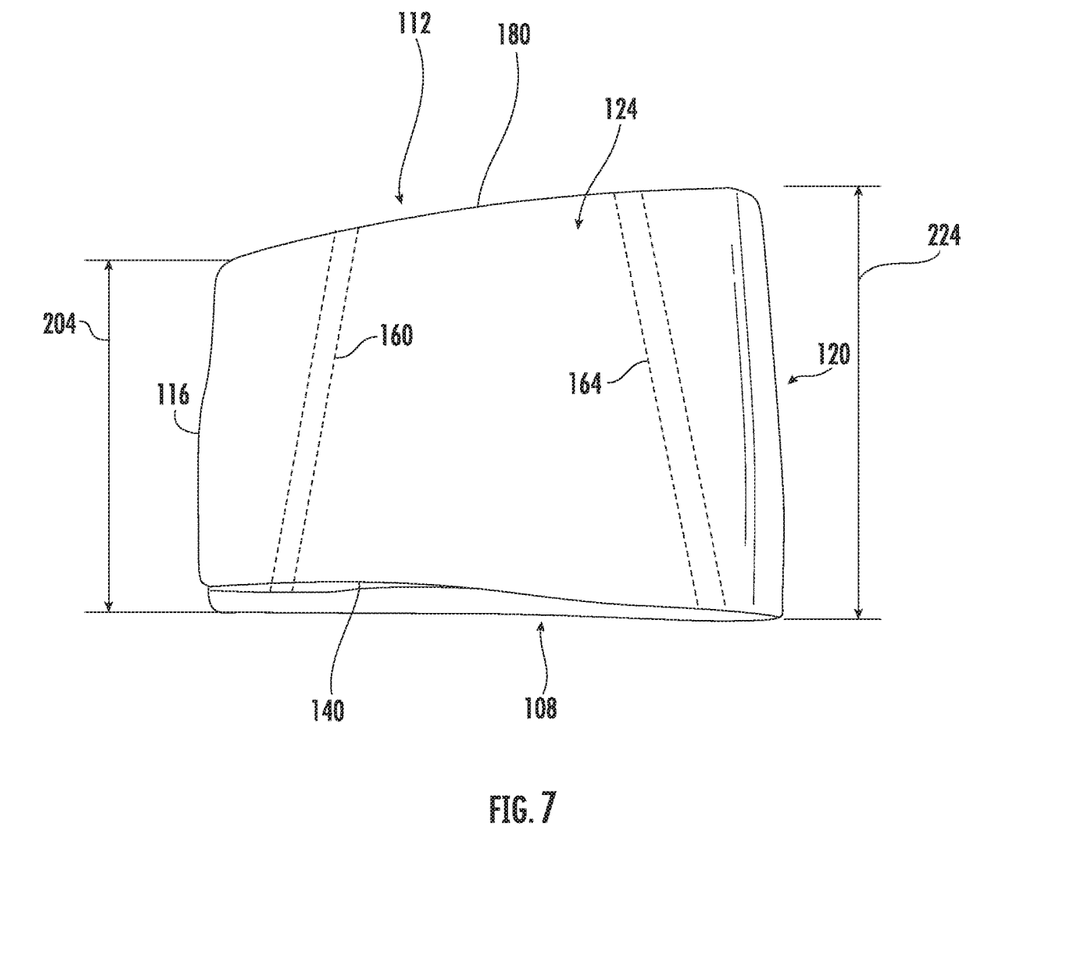
FIG. 7 is a superior view of the midfoot implant of FIG. 1.

Additionally, as best seen in FIG. 7, the lateral side maximum length 224 is less than the largest widths 154, 194 of both the proximal and distal end surfaces 108, 112, but is greater than medial side maximum length 204. Both the lateral and medial side maximum lengths 204, 224 are greater than the largest heights 156, 196 of the proximal and distal end surfaces 108, 112. The reader should appreciate, however, that in other embodiments, the relative dimensions may be different depending on the particular features and functions of the specific midfoot implant.

With continuing reference to FIG. 7, the upper or superior surface 124 of the midfoot implant 100 is defined on its proximal end by the convex superior edge 140 of the proximal end surface 108, and on its distal end by the convex superior edge 180 of the distal end surface 112. Accordingly, the superior surface 124 has a generally convex shape extending laterally across the midfoot implant 100 from the medial side, at which the superior surface 124 transitions smoothly into the medial side surface 116, to the lateral side, at which the superior surface 124 transitions smoothly to the lateral side surface 120.

In the illustrated embodiment, the superior surface 124 is smooth and rounded to accommodate tissue, nerves, muscles, and vascular structures that rest on the superior surface 124 of the midfoot implant 100 without causing discomfort damage to the tissue, nerves, or muscles. In some embodiments, one or more flat or convex channels may be defined in the superior surface 124 so as to accommodate tissues, nerves, muscles, and vascular structures of the foot.

Figure 8:
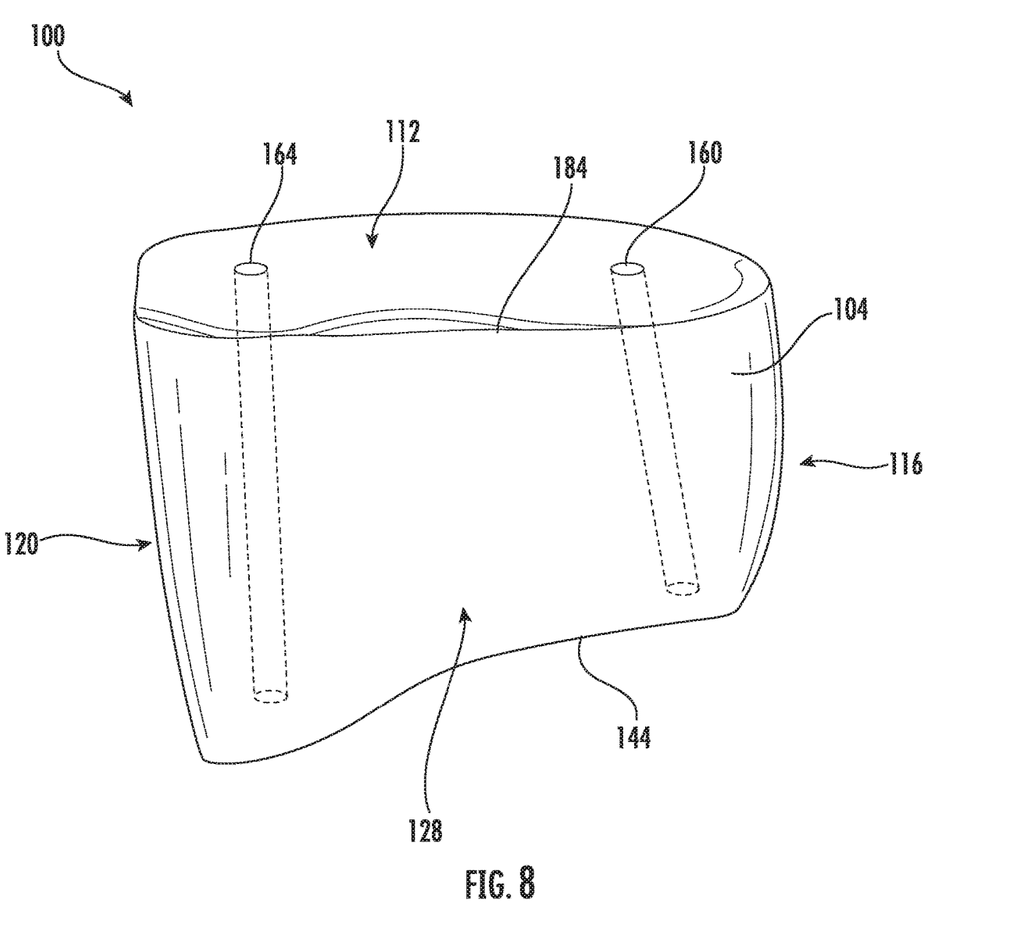
FIG. 8 is a distal-inferior view of the midfoot implant of FIG. 1.

FIG. 8 illustrates the lower or inferior surface 128, which may also be referred to as the plantar surface. The inferior surface 128 is defined at its proximal end by the concave inferior edge 144 of the proximal end surface 108, and at its distal end by the concave inferior edge 184 of the distal end surface 112. The inferior surface 128 is therefore generally concave-shaped, similar to the typical anatomical shape of the plantar region of the midfoot. The medial side of the inferior surface 128 transitions smoothly into the medial side surface 116, while the lateral side of the inferior surface 128 transitions smoothly into the lateral side surface 120. In addition, the inferior surface 128 is smooth and rounded to accommodate tissue, nerves, muscles, and vascular structures that extend beneath the inferior surface 128 of the midfoot implant 100 without causing patient discomfort or damage to the tissue, nerves, or muscles running underneath the midfoot implant 100.

Figure 9:
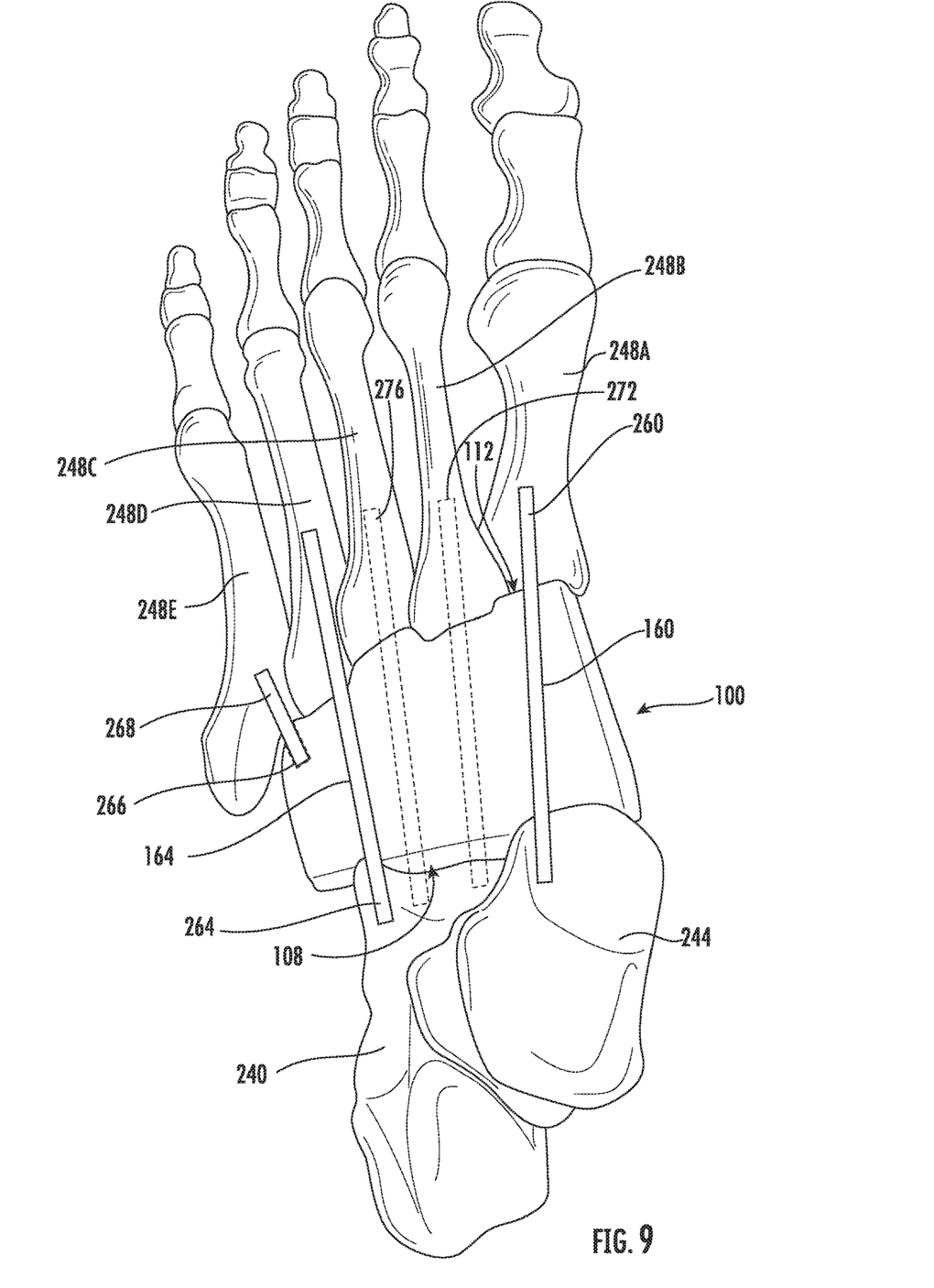
FIG. 9 is a superior view of an adult human foot in which the midfoot implant of FIG. 1 is implanted.
Figure 10:
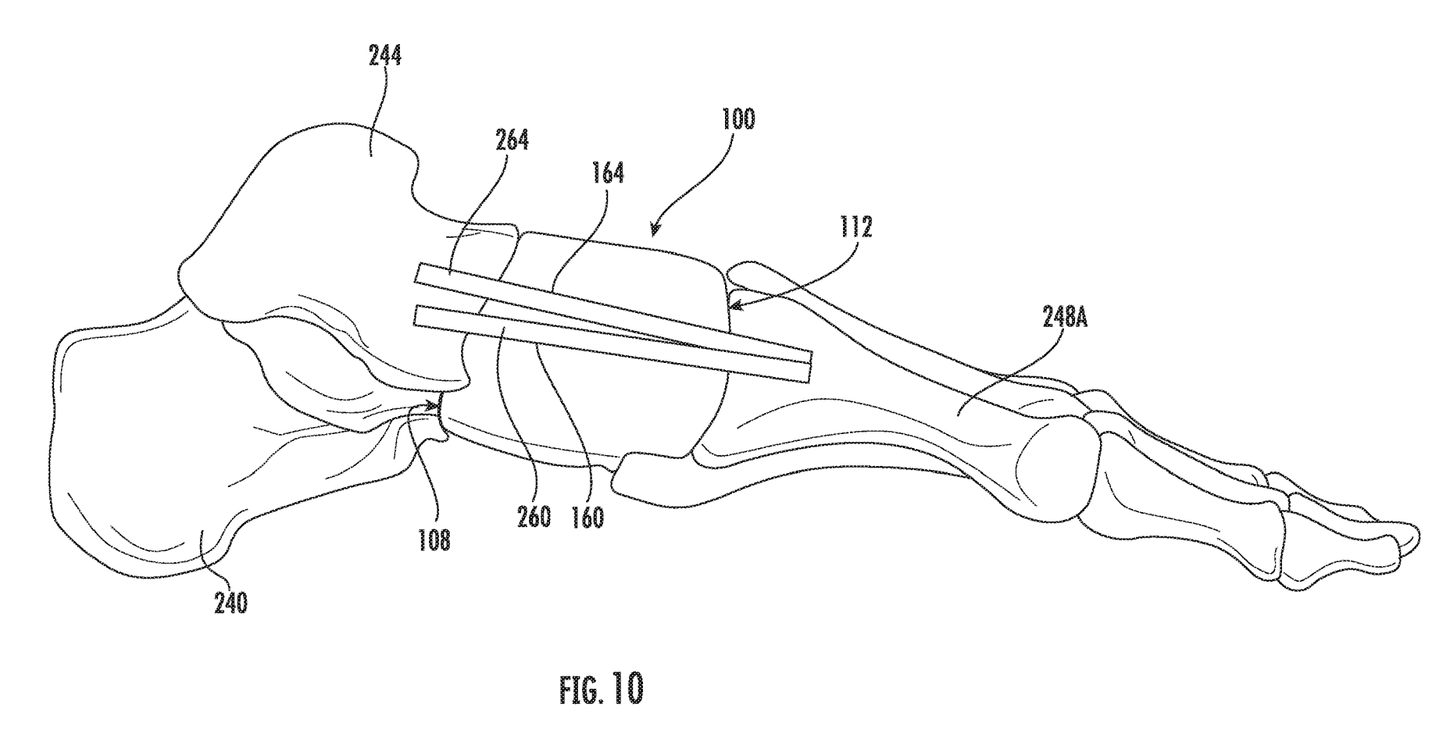
FIG. 10 is a medial side plan view of the adult human foot of FIG. 9 with the midfoot implant of FIG. 1 implanted.

FIGS. 9 and 10 illustrate the midfoot implant 100 in use. The implant 100 is arranged such that the proximal end surface 108 engages the calcaneus 240 and talus 244 bones of the patient's foot, while the distal end surface 112 engages at least the first and fourth metatarsals 248A, 248D. The distal end surface 112 may also engage one or more of the second, third, and fifth metatarsals 248B, 248C, 248E.

A first fixating fastener 260 extends through the medial through-hole 160 and is anchored at its proximal end in the patient's talus 244, and at its distal end in the patient's first metatarsal 248A. A second fixating fastener 264 extends through the lateral through-hole 164 and is anchored at its proximal end in the patient's calcaneus 240, and at its distal end in the patient's fourth metatarsal 248D.

In another preferred embodiment, the midfoot implant 100 further includes a blind hole 266 defined in the lateral outside of the distal end surface 112 or in the distal end region of the lateral side surface 120, extending only partially into the midfoot implant 100. A third fixating fastener 268 affixes the lateral side of the midfoot implant 100 to the fifth metatarsal 248E to provide stability for the fifth metatarsal 248E. Since the peroneus brevis tendon attached to the proximal end of the fifth metatarsal 248E, stabilizing the fifth metatarsal 248E by fixing it to the midfoot implant 100 increases the stability of the patient, thereby improving the patient's ability to walk after implantation of the midfoot implant 100. Accordingly, the embodiment of the midfoot implant 100 that includes the blind hole 266 is particularly effective in improving the patient's mobility.

Additionally or alternatively, the implant may be attached via fourth and/or fifth fixating fasteners 272, 276, which are anchored respectively in the second and third metatarsals 248B and 248C. The fourth and fifth fixating fasteners 272, 276 may extend through through-holes defined in the midfoot implant 100 into the calcaneus 240. Particularly, the fourth and/or fifth fixating fasteners 272, 276 may be used if the first or fourth metatarsals 248A, D are degraded and cannot support the respective first and second fixing fasteners 260, 264. In other embodiments, any combination of the first, second, third, fourth, and/or fifth fasteners 260, 264, 268, 272, 276 may be used.

The fixating fasteners 260-276 may be any desired fasteners, for example solid or cannulated screws, nails, pins, rails, or other surgical fixation devices. Additionally, the third fixating fastener 268 may be shorter than the first and second fixating fasteners 260, 264 since the third fixating fastener 268 does not extend through the entire midfoot implant 100.

Figure 11:
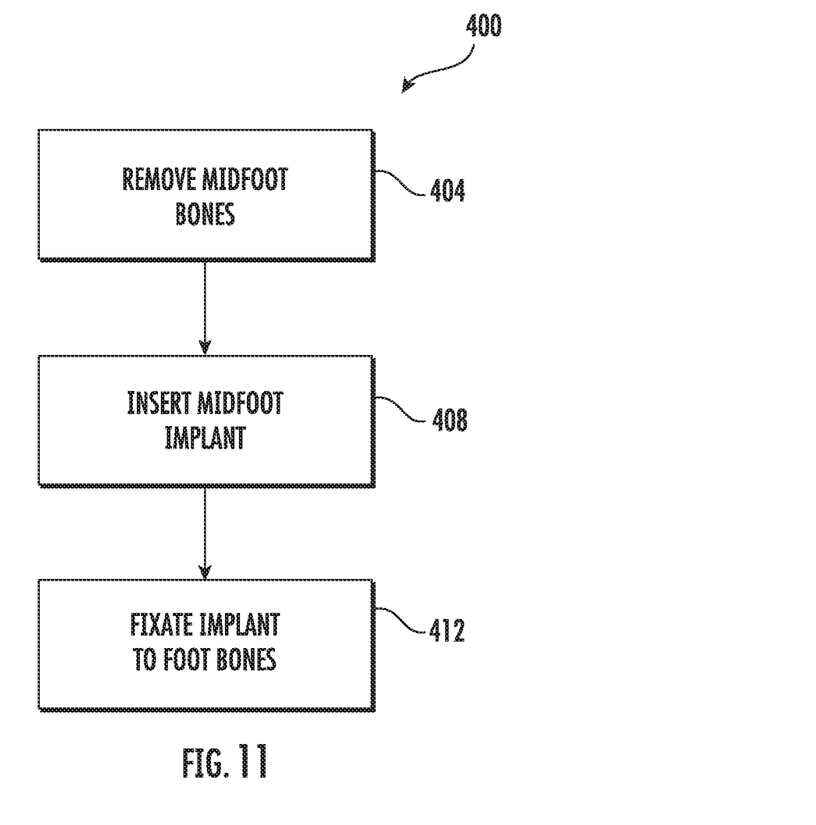
FIG. 11 is a process diagram of surgically implanting a midfoot implant such as the midfoot implant of FIG. 1.

FIG. 11 depicts a process 400 of surgically implanting a midfoot implant such as the midfoot implant 100 described above. The process 400 begins with removing of the cuneiform, navicular, and cuboid bones from the patient's foot (block 404). In some particular embodiments, the cuneiform, navicular, and cuboid bones are removed in their entirety.

The process 400 continues with inserting the midfoot implant 100. More particularly, the midfoot implant 100 is inserted so that the proximal end surface 108 engages the calcaneus 240 and talus 244, while the distal end surface 112 engages at least the first and fourth metatarsals 248A, 248D. Additionally, the surgeon may reposition at least some of the patient's metatarsals 248A-E against the distal end surface 112 in such a way that the patient's overall foot length may be shortened. In particular, in embodiments in which the medial and lateral side maximum lengths 204, 224 are shorter than the average midfoot length, the midfoot implant 100 is usable in a wide variety of patients because little or no harm is caused to the patient by reducing the overall length of the patient's foot.

The process 400 proceeds with fixating the midfoot implant 100 to the bones of the patient's foot. In one embodiment, the fixation includes inserting the first fixating fastener 260 through the first metatarsal 248A and the medial through-hole 160, and into the talus 244 of the patient. The fixation further includes inserting the second fixating fastener 264 through the fourth metatarsal 248D and the lateral through-hole 264, and into the calcaneus 240. The process 400 may further include inserting the third fixating fastener into the blind hole 266 and the fifth metatarsal 248E so as to stabilize the fifth metatarsal 248E.

The midfoot implant is designed to be used with a variety of different patient foot sizes and shapes. Thus, while the through-holes 160, 164 are arranged so as to generally align with the first and fourth metatarsals 248A, 248D, the surgeon may, if necessary, reposition the patient's metatarsals 248A, 248D so that the fasteners align with and can pass through the through-holes 160, 164. The slight alignment adjustment of the patient's metatarsals 248A, 248D causes little or no harm to the patient, and enables the midfoot implant 100 to be usable in a wide variety of patients without the need for custom placement of the through-holes 160, 164.

In the illustrated embodiment, the fixating fasteners 260, 264 are inserted through the first and fourth metatarsals 248A, 248D because the first and fourth metatarsals 248A, 248D are typically aligned with the talus and calcaneus, respectively, and therefore provide a strong connection between the talus 244 and the first metatarsal 248A, and between the calcaneus 240 and the fourth metatarsal 248D. Additionally, as discussed above, it is often desirable for the third fixating fastener 268 to connect the fifth metatarsal 248E to the midfoot implant 100 to stabilize the fifth metatarsal 248E and mitigate any potential damage to the peroneus brevis tendon, which connects to the proximal end of the fifth metatarsal 248E on the lateral side thereof. Optionally, however, the fixation may further include inserting the fourth and/or fifth fixating fasteners 272, 276 through the respective second and/or third metatarsal 248B, 248C and into or through respective holes defined in the midfoot implant 100. In particular, in some embodiments, when the first and fourth metatarsals 248A, 248D are degraded or misaligned, the surgeon may choose to instead or additionally insert the fourth and/or fifth fixing fasteners 272, 276 through the respective second and/or metatarsal 248B, 248C, and into the talus 244 or calcaneus 248.

The fixating fasteners 260-276 may be inserted by any desired known surgical procedure such as, for example, beaming or intramedullary nailing. Once the midfoot implant 100 is fixated to the bones of the patient's foot, the process 400 is complete.

The disclosed midfoot implant 100 replaces the midfoot bones, particularly the cuneiform, navicular, and cuboid bones, in totality or near totality. As a result, the diseased and damaged bones affected by the Charcot foot disease do not remain in the foot. Accordingly, the midfoot implant 100 ensures that the metatarsals are connected to calcaneus and talus with a solid structure that is not at risk of degradation. The likelihood of the patient requiring additional surgeries for the midfoot region, which can increase costs and increase the risk of complications and undesirable patient outcomes, is thus reduced.

Additionally, since the midfoot implant 100 is a solid body 104 formed of a rigid material, the midfoot implant 100 provides improved strength in the patient's foot, reducing the likelihood of subsequent foot injuries in the midfoot region of the patient's foot. Moreover, the improved strength of the midfoot implant 100, in addition to the removal of the potentially damaged bones, allows for a reduction in the recovery time of a patient as compared to a surgery in which some or all of the damaged bones remain in the patient's foot. The patient can therefore engage in physical activities sooner, which improves the patient's overall health. Moreover, the patient is at a lower risk of potential trauma caused by subsequent degradation of the patient's foot to the extent that the patient loses stability and experiences a fall.

Finally, because the midfoot bones are removed in totality or near totality and stabilized by the midfoot implant 100, the risk of further damage to the midfoot bones and the adjacent bones is reduced. As a result, the likelihood of the foot becoming irreparably damaged is reduced, thereby reducing the likelihood that the patient's foot will require amputation.

Figure 12:
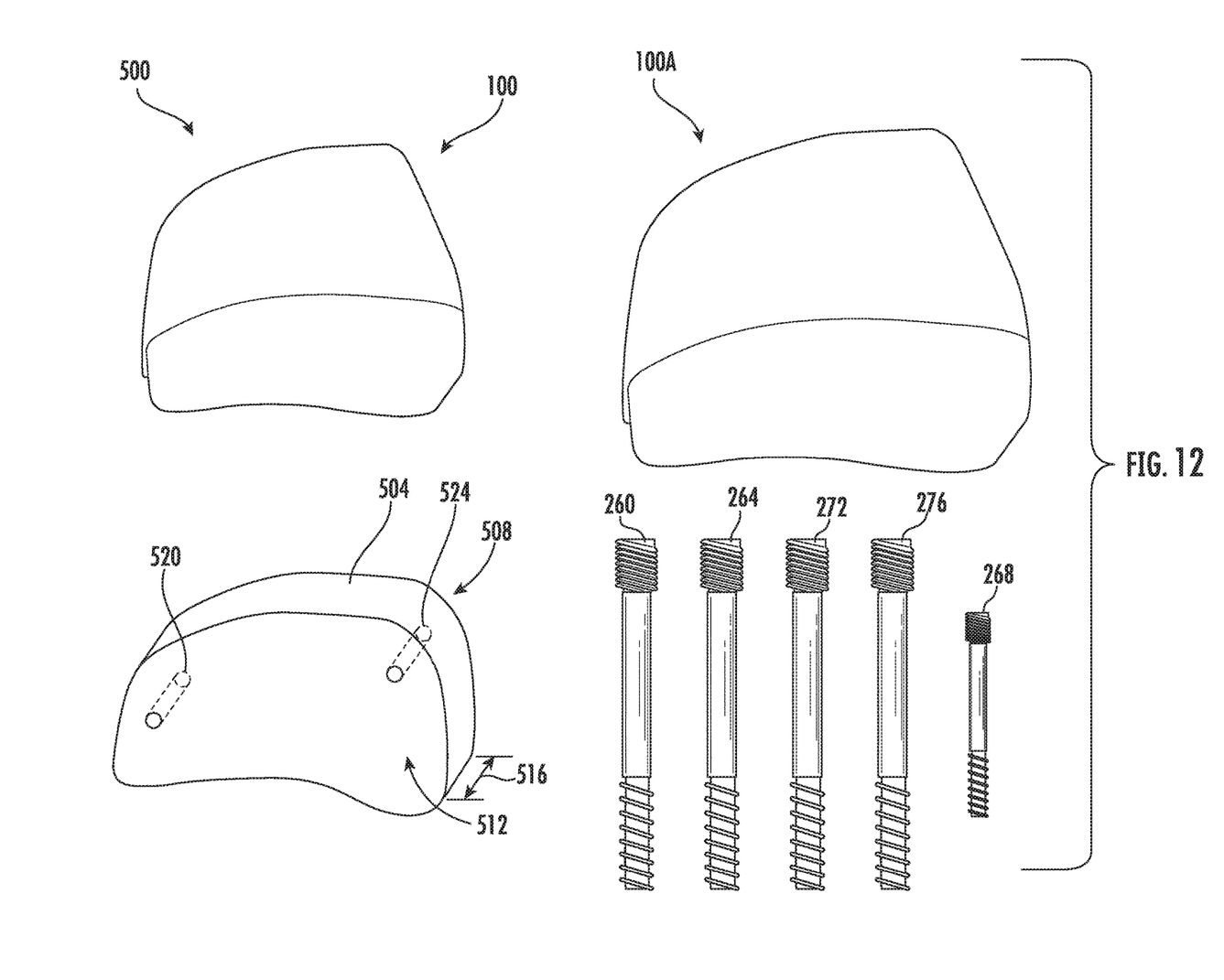
FIG. 12 is a schematic illustration of a kit that includes the midfoot implant of FIG. 1.

The midfoot implant 100 may be packaged in a kit to facilitate surgical implantation in a patient. FIG. 12 illustrates one such kit 500 for repairing damaged midfoot bones in a patient. The kit 500 includes the midfoot implant 100 and the first and second fixating fasteners 260, 264. In a particular embodiment, the kit 500 further includes the third fixation fixating fastener 268, which is shorter than the first and second fixating fasteners 260, 264 so as to fixate the fifth metatarsal 248E into the blind hole 266. In still other embodiments, the kit 500 may include one or both of the fourth and fifth fixating fasteners 272, 276.

In some further embodiments, the kit 500 includes at least one additional midfoot implant 100A, which is similar to the midfoot implant but is sized differently. For example, the additional midfoot implant 100A may have a length in the proximate-distal direction of approximately 1 cm to approximately 3 cm longer than or shorter than the midfoot implant 100, and/or the additional midfoot implant 100A may have a width in the lateral direction of approximately 0.5 to approximately 2 cm greater than or less than the midfoot implant 100.

In another embodiment, the kit 500 may include an embodiment of the implant having two implant pieces, a first piece having a design of implant 100 or implant 100A, and a second implant piece in the form of a spacer 504. The spacer 504 includes two end surfaces 508, 512, each of which has a profile that generally aligns with either the proximal end surface 108 or the distal end surface 112. In another embodiment, one of the end surfaces 508, 512 is larger than the other, and may be larger or smaller than the associated proximal or distal end surface 108, 112. The two end surfaces 508, 512 are spaced apart from one another by a spacer thickness 516. The spacer thickness 516 may be, for example, between approximately 0.5 cm and approximately 2 cm. The spacer 504 also defines through-holes 520, 524, which are configured to align with the through-holes 160, 164 of the midfoot implant 100 so that the fixation fasteners 260, 264 can extend through the spacers 504. In a second embodiment, the spacer 504 may also include another through-hole (not shown) that aligns with the blind hole 266 to allow the third fixating fastener 268 to pass through the spacer 504. The spacer 504 enables the kit 500 to increase the length from the calcaneus and talus to the metatarsals to accommodate feet of various different sizes. In still other embodiments, the implant of the kit may include more than one spacer.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the foregoing disclosure.

The invention claimed is:

1. An implant for a human midfoot, comprising:
a body having a superior surface, an inferior surface, a distal surface, and a proximal surface, the proximal surface configured to engage a talus and a calcaneus of an adult human, the distal surface configured to engage at least first and fourth metatarsals of the adult human, the distal surface having a largest distal height and a largest distal width that is greater than the largest distal height, the proximal surface having a largest proximal height and a largest proximal width that is greater than the largest proximal height;
wherein the largest proximal width is greater than the largest distal width, and the largest proximal height is greater than the largest distal height;
wherein a maximum lateral length is defined from a lateral side of the proximal surface to a lateral side of the distal surface, the maximum lateral length being less than the largest distal width and greater than the largest proximal height; and
wherein a maximum medial length is defined from a medial side of the proximal surface to a medial side of the distal surface, the maximum medial length being less than the maximum lateral length and greater than the largest proximal height.

2. The implant of claim 1, wherein the body defines at least two through-holes extending from the proximal surface to the distal surface.

3. The implant of claim 2, wherein the at least two through-holes includes a first through-hole and a second through-hole, the first through-hole being configured to align at the proximal surface with the talus and at the distal surface with the first metatarsal, and the second through-hole being configured to align at the proximal surface with the calcaneus and at the distal surface with the fourth metatarsal.

4. The implant of claim 3, wherein the midfoot implant is configured to be affixed to the talus and the first metatarsal with a first fixating fastener that extends through the first through-hole, and to the calcaneus and the fourth metatarsal with a second fixating fastener that extends through the second through-hole.

5. The implant of claim 4, wherein the body defines a blind hole extending partially into a lateral side of the distal surface or a lateral surface adjacent to the distal surface, the blind hole configured to receive a third fixating fastener that is configured to affix a fifth metatarsal of the adult human to the implant.

6. The implant of claim 3, wherein a proximal end of the first through hole is located vertically in a middle third of the proximal surface and horizontally spaced apart from a medial edge of the proximal surface by between approximately 5% and approximately 20% of the largest proximal width, and a distal end of the first through hole is located vertically in a middle third of the distal surface and horizontally spaced apart from a medial edge of the distal surface by between approximately 15% and approximately 25% of the largest distal width.

7. The implant of claim 3, wherein a proximal end of the second through hole is located vertically in an upper third of the proximal surface and horizontally spaced apart from a lateral edge of the proximal surface by between approximately 10% and approximately 25% of the largest proximal width, and a distal end of the second through hole is located vertically in a middle third of the distal surface and horizontally spaced apart from a lateral edge of the distal surface by between approximately 15% and approximately 25% of the largest distal width.

8. The implant of claim 1, wherein the body is formed monolithically as a single piece of material.

9. The implant of claim 1, wherein the superior surface has a convex shape and the inferior surface has a concave shape.

10. A kit comprising:
a first implant for a human midfoot, which comprises a body having a superior surface, an inferior surface, a distal surface, and a proximal surface, the proximal surface configured to connect to a talus and a calcaneus of an adult human, the distal surface configured to connect to at least first and fourth metatarsals of the adult human, the distal surface having a largest distal height and a largest distal width that is greater than the largest distal height, the proximal surface having a largest proximal height and a largest proximal width that is greater than the largest proximal height; and
at least two fixating fasteners configured to directly affix the body to the talus, the calcaneus, and the first and fourth metatarsals.

11. The implant of claim 10, wherein the largest proximal width is greater than the largest distal width, and the largest proximal height is greater than the largest distal height.

12. The implant of claim 11, wherein a maximum lateral length is defined from a lateral side of the proximal surface to a lateral side of the distal surface, the maximum lateral length being less than the largest distal width and greater than the largest proximal height.

13. The implant of claim 12, wherein a maximum medial length is defined from a medial side of the proximal surface to a medial side of the distal surface, the maximum medial length being less than the maximum lateral length and greater than the largest proximal height.

14. The kit of claim 10, further comprising:
at least one spacer configured to be interposed between one of (i) the proximal surface and the talus and calcaneus, and (ii) the distal surface and the first and fourth metatarsals.

15. The kit of claim 10, further comprising:
a second implant for the human midfoot, which comprises a second body having a second length, the second length being different from a first length of the first implant.

16. The kit of claim 10, wherein the inferior surface has a concave shape.

17. The implant of claim 10, wherein the body defines at least two through-holes extending from the proximal surface to the distal surface.

18. The implant of claim 17, wherein the at least two through-holes includes a first through-hole and a second through-hole, the first through-hole being configured to align at the proximal surface with the talus and at the distal surface with the first metatarsal, and the second through-hole being configured to align at the proximal surface with the calcaneus and at the distal surface with the fourth metatarsal.

19. The implant of claim 18, wherein the midfoot implant is configured to be affixed to the talus and the first metatarsal with a first fixating fastener of the at least two fixating fasteners that extends through the first through-hole, and to the calcaneus and the fourth metatarsal with a second fixating fastener that extends through the second through-hole.

20. The implant of claim 19, wherein the body defines a blind hole extending partially into a lateral side of the distal surface or a lateral surface adjacent to the distal surface, the blind hole configured to receive a third fixating fastener that is configured to affix a fifth metatarsal of the adult human to the implant.

\* \* \* \* \*